US00PP16564P3

(12) United States Plant Patent
Larsen

(10) Patent No.: US PP16,564 P3
(45) Date of Patent: May 23, 2006

(54) ***OSTEOSPERMUM* PLANT NAMED 'SUNNY ELIZABETH'**

(50) Latin Name: *Osteospermum ecklonis*
Varietal Denomination: Sunny Elizabeth

(75) Inventor: Bjarne Nyholm Larsen, Odense N (DK)

(73) Assignee: Sunny Osteospermum APS, Odense (DK)

( * ) Notice: Subject to any disclaimer, the term of this patent is extended or adjusted under 35 U.S.C. 154(b) by 64 days.

(21) Appl. No.: 10/873,300

(22) Filed: Jun. 23, 2004

(65) Prior Publication Data

US 2005/0022280 P1 Jan. 27, 2005

(30) Foreign Application Priority Data

Jul. 7, 2003 (EM) ..... 2003/1237

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
(74) *Attorney, Agent, or Firm*—Foley & Lardner, LLP

(57) ABSTRACT

A new and distinct cultivar of *Osteospermum* plant named 'Sunny Elizabeth', characterized by its large upright purple inflorescences; ray floret colors: rays have stripes of RHS 155A, white, and RHS 68A red-purple, with base and tip RHS 67A; dense and bushy plant form, mainly due to upright and strong stems, and compact plant habit; and moderately vigorous growth habit, but less need for chemical growth retardation.

4 Drawing Sheets

Genus and species of the plant claimed: *Osteospermum ecklonis* (DC) T. Norl.
Variety denomination: 'Sunny Elizabeth'.

BACKGROUND OF THE INVENTION

The present Invention relates to a new and distinct cultivar of *Osteospermum* plant, botanically known as *Osteospermum ecklonis* (DC) T. Norl., commonly known as Cape Daisy and hereinafter referred to by the variety denomination 'Sunny Elizabeth'.

The new *Osteospermum* is a product of a planned breeding program conducted by the Inventor, Bjarne Larsen, in Stige, Denmark. The new *Osteospermum* originated from a cross made in 2000 by the Inventor between *Osteospermum ecklonis* (DC) T. Norl. designated '9913' (unpatented) and *Osteospermum ecklonis* (DC) T. Norl. designated '90.017.00' (unpatented). The Inventor selected the new *Osteospermum* cultivar from the progeny of the above crossing in 2001 on the basis of its inflorescence color and compact, freely branching habit. Plants of the new *Osteospermum* are upright, compact and have a unique color combination of upper and underside of the ray florets.

Asexual reproduction of the new cultivar by terminal cuttings taken and propagated in trial production batches in Stige, Denmark, has shown that the unique features of this new *Osteospermum* are stable and reproduce true to type in many successive generations.

SUMMARY OF THE INVENTION

The following traits have been repeatedly observed and are determined to be the unique characteristics of 'Sunny Elizabeth'. These characteristics in combination distinguish 'Sunny Elizabeth' as a new and distinct cultivar:

1. Large upright purple inflorescences, ray floret colors: rays have stripes of RHS 155A white, and RHS 68A red-purple, with base and tip RHS 67A;
2. Dense and bushy plant form, mainly due to upright and strong stems, and compact plant habit; and
3. Moderately vigorous growth habit, but less need for chemical growth retardation.

Plants of the cultivar 'Sunny Elizabeth' can be compared to plants of the *Osteospermum ecklonis* (DC) T. Norl. 'Sunny Flora' (unpatented). In side-by-side comparisons conducted by the Inventor in Stige, Denmark, plants of the cultivar 'Sunny Elizabeth' and the cultivar 'Sunny Flora' differ in the following characteristics:

1. Plants of the new *Osteospermum* have striking color combinations of red-purple to pink ray florets and black disk with orange pollen.
2. Plants of the new *Osteospermum* have obovate to spatulate leaves while plants of the cultivar 'Sunny Flora' have obovate to lanceolate leaves.
3. Plants of the new *Osteospermum* have shorter and sturdier grey-purple peduncles while plants of the cultivar 'Sunny Flora' have green peduncles.
4. Plants of the new *Osteospermum* are shorter and more compact due to more branches than the plants of the cultivar 'Sunny Flora'.

Plants of the cultivar 'Sunny Elizabeth' can be compared to plants of the parental cultivars '9913' and '90.017.00'. Plants of the cultivar 'Sunny Elizabeth' differ from plants of the parental cultivars, '9913' and '90.017.00', primarily in inflorescence color.

Plants of the cultivar 'Sunny Elizabeth' have not been observed under all possible environmental conditions. The phenotype may vary somewhat with variations in environment such as temperature, light intensity, day length, and fertility level without, however, any variance in genotype.

BRIEF DESCRIPTION OF THE PHOTOGRAPHS

The accompanying colored photographs illustrate the overall appearance of the new *Osteospermum* cultivar 'Sunny Elizabeth' showing the colors as true as is reasonably possible with colored reproductions of this type. Colors in the photographs may differ slightly from the color values cited in the detailed botanical description which accurately describe the color of the new *Osteospermum* cultivar 'Sunny Elizabeth'.

The first photograph shows a side perspective view of a typical flowering plant of 'Sunny Elizabeth' as grown in an 11 cm pot.

The second photograph shows multiple 'Sunny Elizabeth' plants in the greenhouse.

The third photograph is a close-up, top view of the young and older inflorescences of 'Sunny Elizabeth'.

The fourth photograph shows the detail of front and back of 'Sunny Elizabeth' inflorescences as well as the front and back of the leaf.

DETAILED BOTANICAL DESCRIPTION

In the following description, color references are made to The Royal Horticultural Society Colour Chart (R.H.S.), 4$^{th}$ edition. Plants were grown under greenhouse conditions. Plants used for this description were grown for about 20 weeks after cutting.

Botanical classification: *Osteospermum ecklonis* (DC) T. Norl.

Parentage:

*Female parent.*—*Osteospermum ecklonis* (DC) T. Norl. designated '9913' (unpatented).

*Male parent.*—*Osteospermum ecklonis* (DC) T. Norl. designated '90.017.00' (unpatented).

*Propagation.*—Type cutting: terminal vegetative cuttings.

*Time to initiate roots.*—About 10 to 14 days at 18 to 21° C. in tunnels in a greenhouse.

*Root description.*—Fine, well branched.

Plant description:

*Form.*—Perennial plant with upright plant habit. *Osteospermum* flowers in composite capitulate. Freely branching with lateral flowering branches forming at every node; dense and bushy.

*Crop time.*—After rooting, about 18 weeks are required to produce finished flowering plants in 11 cm pots.

*Plant height* (*soil level to top of plant plane*).—About 16 cm.

*Plant diameter.*—21 cm.

*Vigor.*—Moderately vigorous growth rate.

Foliage description: Leaves alternate, single, 4–6 lobed, close to pinnate venation. Length: 3–6 cm. Width: About 35 mm. Shape: Obovate to spatulate. Apex: obtuse. Base: attenuate. Margin: broadly lobed. Texture: smooth, glabrous, shiny. Scattered short, stiff hairs. Color: Young foliage, upper and lower surfaces: RHS 146B to 146C, yellow-green. Mature foliage, upper surface RHS 147A, yellow-green, lower surface RHS 147B. Venation, RHS 148A, yellow-green.

Inflorescence description:

*Inflorescence arrangement and shape.*—Tubular disk and ligulate ray flowers in composite daisy heads; with 15 parted involucre.

*Natural flowering season.*—Continuous throughout the spring and summer. Season can be extended by vernalization and long day treatments.

*Inflorescence longevity on the plant.*—5 to 9 days (longevity of individual inflorescences is highly dependent on temperature and light conditions). Inflorescences persistent, ray florets folding and withering slowly to RHS N187B, gray-purple.

*Inflorescence diameter.*—About 6 cm.

*Inflorescence depth.*—Typical: 12 mm. Observed: Composite capitulum 10–14 mm.

*Inflorescences.*—Ray Florets: Typical number of ray florets per inflorescence: 25. Observed number of ray florets per inflorescence: 22–26. Length: Ray florets: About 27 mm. Width (diameter): About 8 mm. Ray floret apex: lanceolate, slightly retuse. Ray floret base: Fused. Ray floret margin: entire. Ray floret color: Upper surfaces (when opening): stripes of RHS 155A, white, and RHS 68A, red-purple, base and tip: RHS 67A, red-purple; under side (when opening): stripes of RHS N77C, purple, and RHS 65C, red-purple (pink). Upper surfaces (fully opened): stripes of RHS 62D, red-purple, and RHS 70B, red-purple; under sides (fully opened): stripes of RHS N77C, purple, and RHS 69C, light red-purple.

*Disk florets.*—Typical number of disks florets per inflorescence: 75. Observed number of disks florets: 60–80. Length: Disk florets: About 4 mm. Width (diameter): About 2 mm. Disk floret overall shape: tubular. Disk floret tip/apex: attenuate. Disk floret base: fused. Disk floret margin: entire. Disk floret color: Upper surfaces: RHS N89B, violet-blue. Abaxial surfaces: Tips RHS N89A, violet-blue and bases RHS 65D, red-purple.

*Peduncle.*—Strength: Moderately strong. Length: About 6 cm. Diameter: About 3 mm. Color: Base 144A yellow-green, apical 2 cm N187A, grey.

*Phyllary.*—Observed number of phyllaries: 20. Typical number of phyllaries: 20. Length: 9–12 mm. Width: 3–4 mm. Overall shape: lanceolate. Apex shape: acuminate. Base shape: fused. Margin: entire, translucent. Color: Upper surface: RHS 138D, green; lower surface: RHS 138B, green.

Reproductive organs:

Androecium:

*Location.*—Disc florets only.

*Anthers. Linear, fused, stamen color RHS* 202A, black, filament.—RHS N155B, white.

*Pollen.*—RHS N25A orange.

Gynoecium:

*Location of gynoecium.*—Ray and disc florets.

*Pistil and stigma.*—Typical pistil number: 1. Observed pistil number: 1. Stigma color: RHS N187A, purple.

*Style.*—RHS N155B, white.

*Seed.*—Length about 1 mm, diameter about 0.3 mm.

Disease/pest resistance: Good.

Disease/pest susceptibility: Low.

Weather tolerance: Plants of the new *Osteospermum* have exhibited good tolerance to draught, rain and wind. Temperature tolerance −1° C. (30° F.).

I claim:

1. A new and distinct cultivar of *Osteospermum* plant named 'Sunny Elizabeth', as illustrated and described herein.

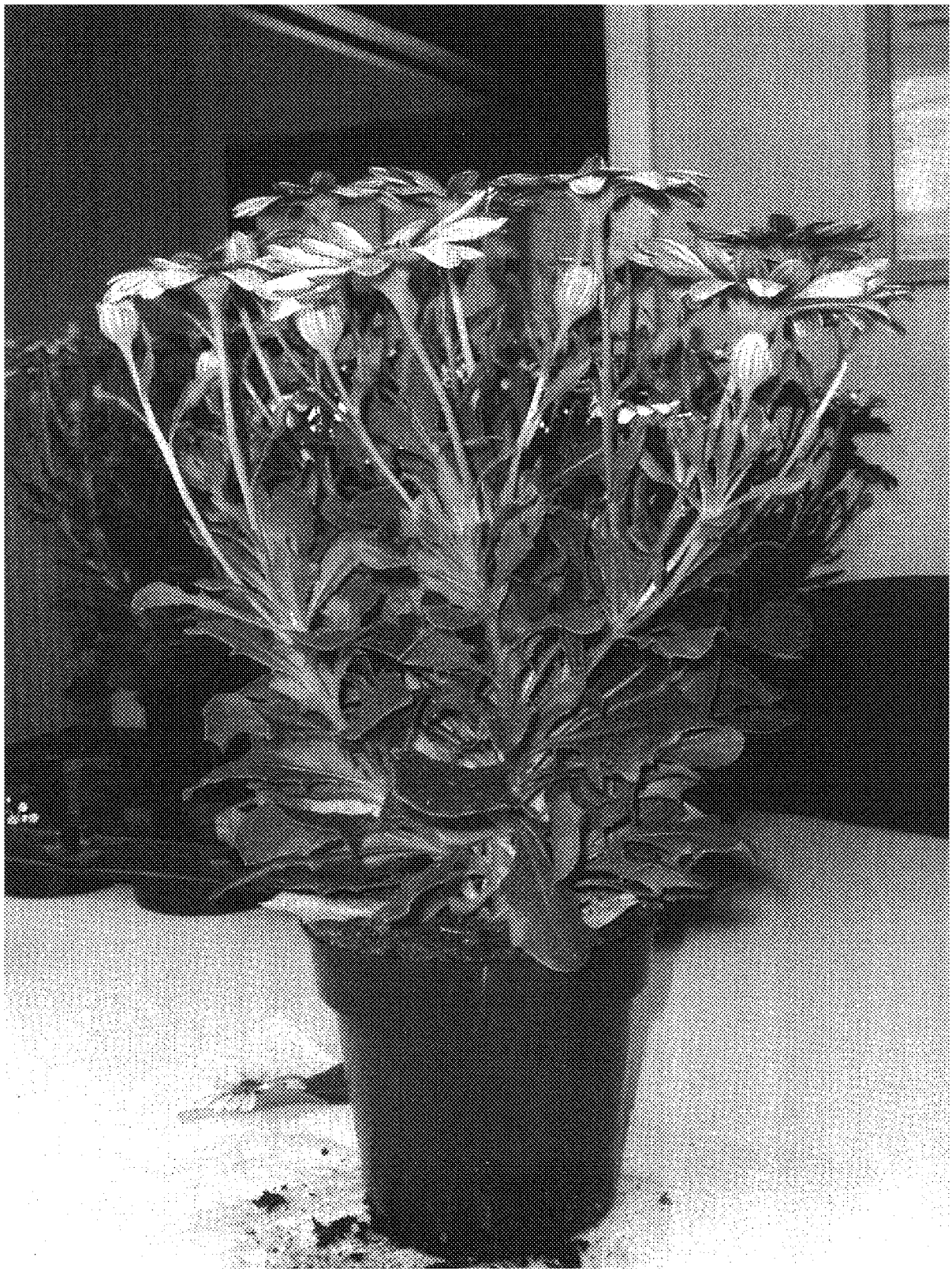

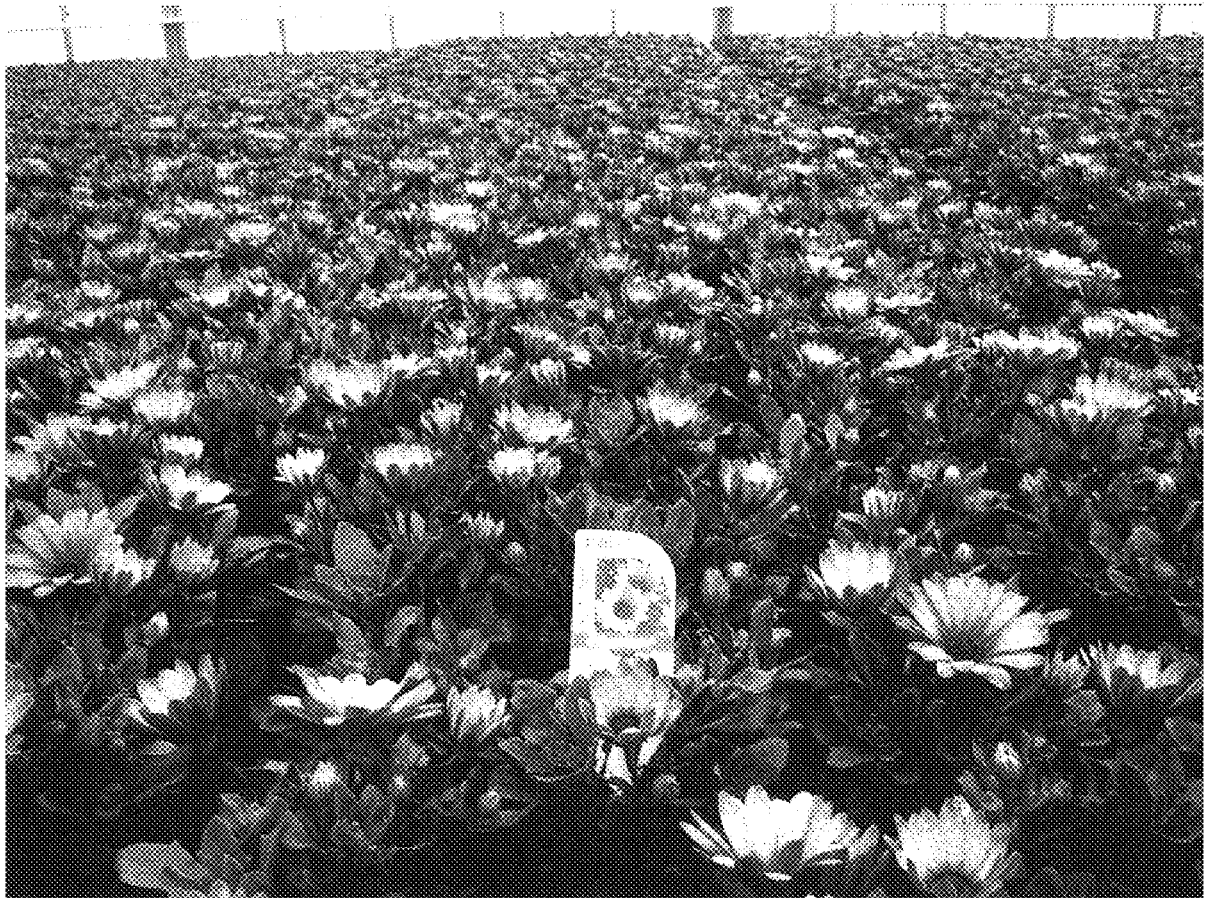

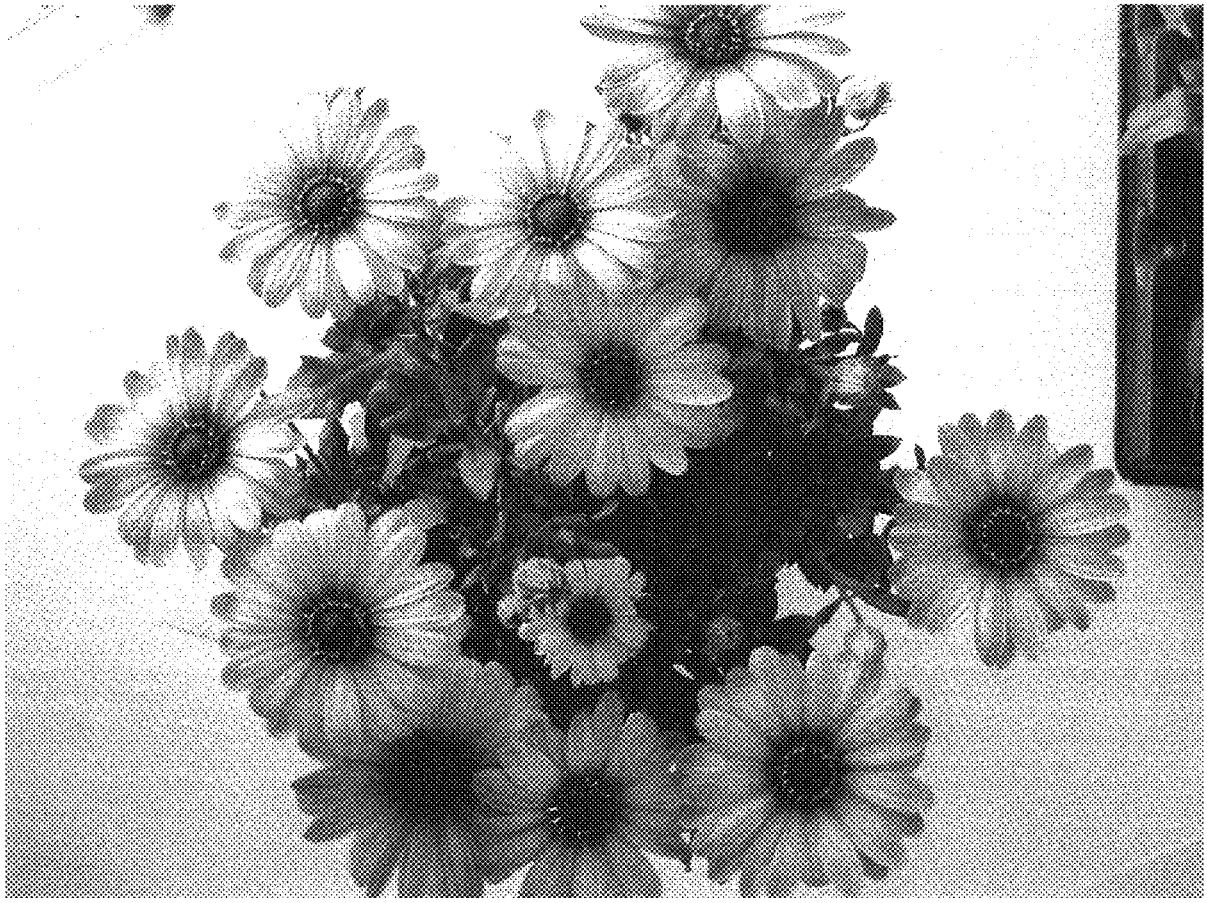

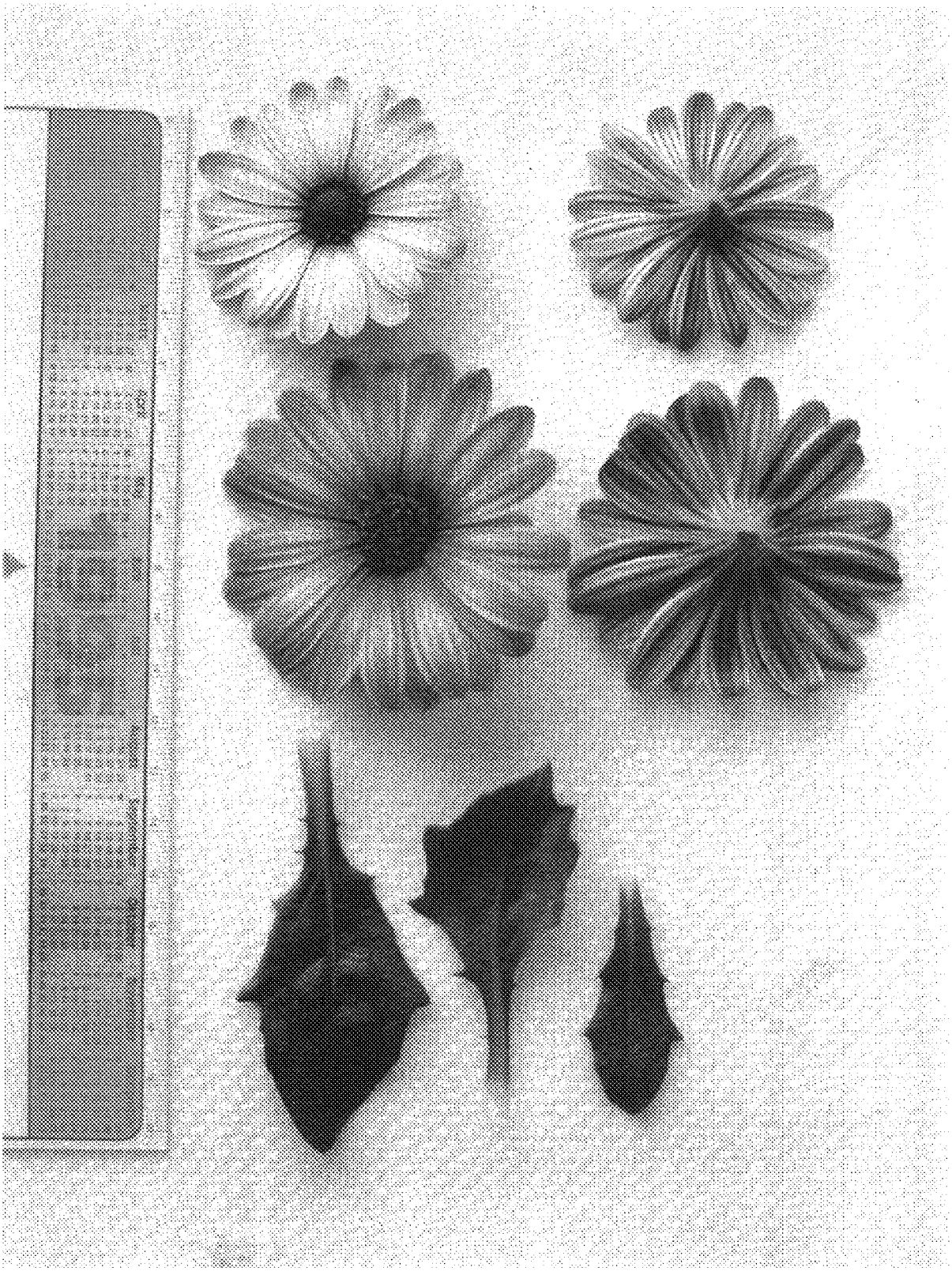

* * * * *